(12) United States Patent
Ellis et al.

(10) Patent No.: US 8,038,723 B2
(45) Date of Patent: Oct. 18, 2011

(54) EPILATORY COMPOSITIONS

(75) Inventors: Paul Ellis, Hull (GB); Philippe Henriat, Chartres (FR); Natalie Thomas, Montvale, NJ (US); Isabelle Rigal, Hull (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 0 days.

(21) Appl. No.: 12/448,716

(22) PCT Filed: Feb. 19, 2008

(86) PCT No.: PCT/GB2008/000571
§ 371 (c)(1),
(2), (4) Date: Oct. 30, 2009

(87) PCT Pub. No.: WO2008/102125
PCT Pub. Date: Aug. 28, 2008

(65) Prior Publication Data
US 2010/0146715 A1  Jun. 17, 2010

(30) Foreign Application Priority Data
Feb. 19, 2007 (GB) .................................. 0703176.8

(51) Int. Cl.
*C14C 99/00* (2006.01)
(52) U.S. Cl. .................................. 8/94.16; 8/160; 8/161
(58) Field of Classification Search .................... 8/94.16, 8/160, 161
See application file for complete search history.

(56) References Cited

U.S. PATENT DOCUMENTS

| 7,005,557 B2 * | 2/2006 | Klofta et al. ................. 604/360 |
| 2005/0079189 A1 | 4/2005 | Archer et al. |
| 2007/0031360 A1 | 2/2007 | Gupta |

FOREIGN PATENT DOCUMENTS

| GB | 2 369 573 A | 6/2002 |
| GB | 2 385 269 A | 8/2003 |
| GB | 2 446 576 A | 8/2008 |
| GB | 2385269 | * 8/2008 |
| WO | WO 02/11687 A | 2/2002 |
| WO | WO 2005/112876 A | 12/2005 |
| WO | WO 2008/102125 A1 | 8/2008 |

OTHER PUBLICATIONS

PCT International Search Report, PCT/GB2008/00571, dated Jul. 2, 2008.
UK Combined Search and Examination Report, GB0703176.8, dated May 29, 2007.
U.S. Appl. No. 11/991,676, filed Jan. 12, 2009, Inventor: Ellis et al., Title: Improvements in or Relating to Cosmetic Compositions.
U.S. Appl. No. 12/083,470, filed Sep. 29, 2008, Inventor: Archer et al., Title: Microemulsion and Shaving Apparatus Comprising a Microemulsion.

* cited by examiner

*Primary Examiner* — Amina Khan
(74) *Attorney, Agent, or Firm* — Ryan A. Schneider; Troutman Sanders LLP

(57) ABSTRACT

An epilatory composition, substantially provided as flat strips, comprises a gel-like matrix material, for example a rosin-based or sugar-based material and, mixed with the matrix material, a particulate material, for example colloidal particles of fumed silica, and a polyethylene in the form of a homopolymer. The particles reduce the tendency of the epilatory composition to flow, under warm ambient conditions with improved efficacy over known epilatory compositions.

9 Claims, No Drawings

EPILATORY COMPOSITIONS

This invention relates to an epilatory composition, its manufacture and use.

Epilatory compositions formed of viscoelastic materials are well known. The viscoelastic materials may in certain embodiments be rosin-based. In other embodiments they may be sugar-based. A tackifier, such as colophony, may be included to make them sticky.

In some products the epilatory compositions may be supplied in the form of strips, retained between cellophane or woven sheets. The cellophane sheets may have coatings of polyvinyl chloride, which acts as a barrier preventing the composition, or components of it, from migrating through the sheets; and also having the correct adhesive properties for use. In use, the user peels away one of the cellophane sheets, presses the epilatory strip firmly onto the area to be plucked, then pulls one end of the remaining sheet sharply away from the area. The hairs trapped in the composition are removed from the treated area along with, optimally, all of the composition, still attached to the remaining backing strip.

In an alternative approach a composition may be warmed, and then applied to the skin by means of a spatula or other applicator. Strips of fabric are then applied so that they adhere to the epilatory composition. The strips are then pulled sharply to remove the epilatory material, and hair, from the skin.

In both approaches the viscoelastic properties of the compositions are important. However this is particularly so in the case of the compositions supplied as strips, since these are applied to the skin at ambient temperature. At ambient temperature the compositions should be soft and pliable, such that they mould closely to the body shape. On the other hand they must not be so soft that they flow prior to use. When they are in place on the body and the user pulls the remaining backing strip, applying a high frequency strain rate to the compositions, their elastic properties should predominate over their viscous properties.

There is a particular problem with known compositions supplied in the form of strips, in meeting one of the requirements described in the previous paragraph. It is, that under warm ambient conditions the compositions may flow, and leak out from between the sheets. One approach to counter this has been to supply strips with considerably over-sized cellophane sheets. However, clearly, this approach is inadequate as a solution to a situation where there might be a substantial flow of a composition. It is also inefficient in terms of materials and transportation, and undesirable from a marketing perspective, in that consumers perceive that such a product is of poor value.

Accordingly, there is a need for an epilatory composition with improved resistance to flow of the composition, in warm environments, prior to use.

In accordance with a first aspect of the present invention there is provided an epilatory composition comprising an admixture of a matrix rosinous or sugar-based material, particulate silica, and a polyethylene in the form of a homopolymer.

It has been found that the addition of a polyethylene in the form of a homopolymer to an epilatory composition with a resin mix and silica substantially improves the hair removal efficacy of the composition when compared to other polymers known in the art, for example polyisobutane or $C_{1-4}$ polyalkylene. The efficacy is especially improved when the epilatory formulation is in a cold wax strip format. It has also been observed to improve the stability of the wax on strips, and the resistance to flow under warm conditions.

Preferably the polyethylene has a molecular weight from 100 to 1000, preferably from 250 to 800 more preferably from 300 to 600 unified mass units. This gives the advantage of ease of incorporation of the polyethylene into the hydrophobic particles of the invention by melting and blending. Polyethylene suitable for use in compositions of the invention is a substantially linear or non-branched polymer with the structure $CH_3CH_2(CH_2CH_2)_nCH_2CH_3$, where n is a mean number from 2 to 26, preferably from 5 to 15. Preferably at least 90% by weight of the polyethylene is linear or non-branched. A particularly preferred polyethylene is that sold under the registered trade name Performalene. Other suitable polymers include polybutene grades, ethylene and vinyl acetate, piperylene/butane/pentene/pentadiene copolymer, goovean fibre viscose, however performalene is preferred.

The polyethylene is typically present in an amount in the range 0.1% to 5% by weight of the composition. Preferably, 0.5% to 4.0%, more preferably 0.5% to 3.0% by weight of the composition. However, a particularly preferred amount is in the range 0.75% to 1.5%, such as around 1.0% by weight of the composition.

It is desirable that the ratio of the silica to polyethylene is in the range 16:1 to 2:3. Preferably the ratio of silica to polymer or co-polymer is in the range 6:1 to 6:5. A particularly preferred ratio is in the range 2:1.

The matrix material is suitably a gel-like material with adhesive properties.

Preferably, however, the matrix material comprises a tackifying rosinous material, for example a rosin ester and/or colophony.

Preferably the epilatory composition comprises at least 60% wt/wt of rosinous material, preferably at least 70% wt/wt, more preferably at least 80% wt/wt.

Preferably the epilatory composition is a so-called "cold" epilatory composition (that is, one which can be applied at ambient temperature without reheating).

Typically, the particulate silica is fumed silica. Preferably the particulate fumed silica is a colloidal material. Preferably it has particles of mean diameter 1-200 nm, more preferably 5-100 nm, and most preferably 10-50 nm.

Preferably the particles are present in the matrix material in an amount of at least 0.5% wt/wt, more preferably at least 1.0% wt/wt, and most preferably at least 1.5% wt/wt. Suitably they are present in an amount up to 10% wt/wt, preferably up to 8.0% wt/wt, and most preferably up to 6.0% wt/wt. It is particularly preferred that the particulate silica is present in an amount substantially about 2.0% by weight of the formulation.

Fumed silica is currently manufactured in a process that involves flame hydrolysis of silicon tetrachloride, in an oxyhydrogen flame. It is a colloidal form of silica having silanol groups, able to participate in hydrogen bonding. Fumed silica typically comprises colloidal particles of mean diameter 1-200 nm. Preferably the fumed silica is of mean diameter 5-100 nm, more preferably 10-50 nm. The external surface area is typically in the range 15-380 $m^2/g$. Fumed silicas are typically non-porous and thus have no internal surface area. They may be hydrophobic and of use in the present invention but preferred fumed silicas for use in the present invention are hydrophilic.

The epilatory composition may suitably comprise up to 40%, preferably up to 20%, of other components, which may include one or more of a natural wax, a fragrance, a polymer, an essential oil, a silicone oil, a colorant, an anti-oxidant or a paraffin or mineral oil.

Suitably an epilatory composition comprising a rosinous material, when formed into sheets and not under applied stress, is shape-stable for a period of 6 months at all temperatures in the range 20-50° C.

Suitably an epilatory composition comprising a rosinous material, when formed into sheets and not under applied stress, is shape-stable for a period of 6 months at all temperatures in the range 20-50° C.; whereas the corresponding matrix material not containing any said particles, when formed into flat sheets and not under applied stress, flows under its own weight at least some temperatures in the range 20-50° C. during a period of 6 months.

Suitably the epilatory composition is such that its elastic modulus exceeds its viscous modulus at all frequencies up to 0.1 rad/s at 50° C.

Preferably the elastic modulus of the epilatory composition exceeds its viscous modulus at all frequencies up to 1 rad/s at 50° C., more preferably at all frequencies up to 2 rad/s at 50° C.

In certain embodiments, notably epilatory compositions having a sugar-based matrix material, the elastic modulus may exceed the viscous modulus at all frequencies up to 20 rad/s at 50° C.

Preferably at certain higher frequencies (representative of the rapid removal of the epilatory composition from the user's skin), the elastic modulus also exceeds the viscous modulus, at temperatures within the temperature range 20-50° C.

Preferably the elastic modulus exceeds the viscous modulus (when measured at 35° C.) at a frequency of at least 10,000 rad/s, more preferably at a frequency at least 5,000 rad/s.

Thus, preferably the epilatory composition is such that, at ambient temperatures, at low frequencies of applied stress the elastic modulus exceeds the viscous modulus; at high frequencies of applied stress the elastic modulus exceeds the viscous modulus; and at moderate frequencies, in between, the viscous modulus exceeds the elastic modulus. The epilatory composition in transit and storage corresponds to the low frequency condition, and the non-viscous nature of the composition aids shape stability in storage and transit; the application of the epilatory composition to the skin corresponds to the moderate frequency condition, and the viscous nature of the composition aids application and good contact with hair and skin; and pulling the epilatory composition sharply from the skin corresponds to the high frequency condition, the non-viscous, glassy nature of the composition aiding effective hair removal. The transition between the low frequency condition and the moderate frequency condition is known as the gel point. The transition between the moderate frequency condition and the high strain rate condition is known as the glass transition.

The elastic modulus G' (sometimes known as the storage modulus) corresponds to the energy which can be stored and released by a bulk material. The viscous modulus G" (sometimes known as the loss modulus) corresponds to the energy dissipated by a bulk material due to friction between its macromolecules when it is deformed.

$$G' = \frac{\sigma.\cos\delta}{\gamma}$$

$$G'' = \frac{\sigma.\sin\delta}{\gamma}$$

wherein $\sigma$. is the stress amplitude, $\gamma$. is the strain amplitude and $\delta$ is the out-of-phase coefficient.

The measurements quoted later are based on studies carried out into the rheology of the viscoelastic compositions in order to obtain a better understanding of their adhesive behaviour and their suitability as epilatory materials. These studies involved subjecting the materials to dynamic investigations in which a sinusoidal strain at defined frequencies was applied to the materials and the resulting output force was measured. In these studies a stress control rheometer was used, the SR rheometer commercially available from the company Rheometrics, using parallel plate geometry of 25 mm in diameter. The output force was found to include an in-phase elastic component G' and an out-of-phase viscous component G". The output force can be expressed as follows.

$$\sigma = \sigma.\sin(t\omega + \delta)$$
$$= \sigma. \cos\delta\sin t\omega + \sigma. \cos\delta\cos t\omega$$

where $\omega$ is the test frequency and t is the time.

Within the linear stress-strain domain of the material G' is desirably lower than G" at moderate frequency oscillation in order to prevent the material cracking and to ensure that the material has strong adhesion at the material/hair interface. The values of G' and G" at moderate frequency oscillation are a measure of how readily the material wets the hairs. Moderate frequency oscillation is a long time process and corresponds to the time when the material is being applied to the skin. The lower values of G' and G" at this moderate frequency, the better the material wets the hairs. Thus the hairs become well embedded in the material in a very short time (ie the time needed for spreading the material on the skin). However G' should be higher than G" at high frequency oscillation (which mimics the action of the user in rapidly pulling the strip from the body) in order to remove hairs efficiently. Also, at low frequency oscillation, or no oscillation, G' is preferably higher than G", in accordance with this invention, in order to obtain the benefit of enhanced stability, even when warm.

The definitions given herein refer to stresses applied to the material within its linear stress-strain domain, which may typically be up to a few thousand Pa.

By ensuring that the epilatory composition satisfies the above parameters, it can be readily applied to the skin at body temperature, yet it is very efficient at removing hairs from the skin and, surprisingly, the user experiences less pain.

References in this specification to a material not under applied stress are to a material in the form of a flat sheet, resting on a horizontal surface.

Whilst we are not bound by any theory, we believe that the particles form a network throughout the epilatory composition, providing a structure or backbone which inhibits the flow of the composition, at warm temperatures.

If wished the epilatory composition of the present invention may be provided in a container, from which the user removes it using, for example, a spatula or an applicator fitted to the container, and applies it to the skin. A fabric can then be used to pull the applied material in one piece from the skin. Alternatively, and preferably, the epilatory composition is supplied in the form of strips, sandwiched between sheets, for example of cellophane, or paper or another non-woven material. In use, one sheet is removed from a strip of epilatory composition and that strip is then applied to the skin with the remaining sheet uppermost. The end of that sheet is grasped and pulled sharply, to remove the strip of epilatory composition from the skin, along with hairs with which it is in contact.

Because the epilatory composition does not flow even under very warm ambient conditions it may be applied to a sheet during manufacture so as to cover a larger area of the sheet, than has been achieved, with prior epilatory compositions. Preferably it covers at least 60% of the area of the sheet, more preferably at least 80%, most preferably at least 90%.

In accordance with a further aspect there is provided an epilatory product, comprising epilatory strips formed of an epilatory composition as defined herein, the epilatory strips being sandwiched between sheets which are peelable from the strips.

In accordance with a further aspect there is provided a method of epilation, using a composition or product of the invention.

The invention will now be further described, by way of example.

EXAMPLE 1

A composition was made with the following ingredients.

| Ingredients | % wt/wt |
|---|---|
| triethylene glycol rosinate | 64.777% |
| Glyceryl rosinate | 31.803% |
| Silica | 1.95% |
| polyethylene | 1.05% |
| Perfume | 0.3% |
| BHA | 0.01% |
| Cosmetic Ingredient | 0.1% |
| Dye | 0.014% |

The composition is manufactured as follows:

1. The performalene is melted at a temperature of approx 100° C. The silica is then dispersed inside the resin mix. The melted performalene is incorporated into the resin mix with silica. This admixture is then transferred to a second tank. The remaining ingredients are then added to the second tank and blended to form the final epilatory composition.

Panel Study 1:

Hair removal using the product manufactured in example 1 was assessed by counting the hairs before waxing, applying the wax strips and counting hair after waxing. Hair removal % for the formula given in Example 1 was at least 10% higher than with no polyethylene in the form of a homopolymer.

Panel Study 2:

A similar methodology was followed as with panel study 1, Hair removal of proposed formula was at least 8% superior to a formula with no polyethylene in the form of a homopolymer. Although not significant difference was obtained, it showed directional improvement in hair removal. It was also qualitatively noted during the test that the proposed formulae left less residues vs. one with no polyethylene.

Perceived efficacy of proposed formula was also high and obtained at least 8/10 score with 20 panelists.

Stability

Different formulae were put in stability at 60 deg C. for 1 week, and leakage was assessed. The composition of the present invention had no leakage. It has been observed that, under storage conditions, the composition of the present invention has lower spreadability than one with no polymer/copolymer.

The invention claimed is:

1. An epilatory composition comprising:
    a rosinous or sugar-based matrix material in admixture with a particulate colloidal silica present in an amount up to 10% wt/wt of the epilatory composition, and
    a polyethylene in the form of a homopolymer, wherein the polyethylene is substantially linear or non-branched, has a molecular weight from about 250 to about 800 unified mass units, and is present in an amount in the range 0.1% to 5% by weight of the composition,
    wherein the ratio of silica to polyethylene the epilatory composition is in the range 6.0:1.0 to 6.0:5.0 and wherein at least 60% of the weight of the epilatory composition is provided by rosinous material.

2. An epilatory composition according to claim 1, wherein the polyethylene is a substantially linear polymer with the structure $CH_3CH_2(CH_2CH_2)_nCH_2CH_3$, where n is a mean number from 2 to 26.

3. An epilatory composition according to claim 2, wherein at least 90% by weight of the polyethylene is linear.

4. An epilatory composition according to claim 1, wherein, the polyethylene is present in an amount in the range 0.5% to 4.0% by weight of the composition.

5. An epilatory composition according to claim 4, wherein the polyethylene is present in an amount in the range 0.5% to 3.0% by weight of the composition.

6. An epilatory composition according to claim 1, wherein the particulate silica is fumed silica.

7. An epilatory composition according to claim 1, wherein the particulate silica is present in an amount of about 2.0% by weight of the formulation.

8. An epilatory composition according to claim 1, wherein when formed into sheets and not under applied stress, is shape-stable for a period of 6 months at all temperatures in the range 20-50° C.

9. An epilatory product comprising epilatory strips formed of an epilatory composition according to claim 1, the epilatory strips being sandwiched between sheets which are peelable from the strips.

* * * * *